US012622881B2

(12) United States Patent
Vona et al.

(10) Patent No.: US 12,622,881 B2
(45) Date of Patent: May 12, 2026

(54) WATER-SOLUBLE TOPICAL OPHTHALMIC PREPARATION CONTAINING LUTEIN AND PRODUCTION METHOD THEREOF

(71) Applicant: Omisan Farmaceutici S.R.L., Guidonia Montecelio (IT)

(72) Inventors: Nevio Vona, Guidonia Montecelio (IT); Walter Quattrocchi, Guidonia Montecelio (IT); Giuseppe Del Vecchio, Guidonia Montecelio (IT)

(73) Assignee: OMISAN FARMACEUTICI S.R.L, Guidonia Montecelio (IT)

( * ) Notice: Subject to any disclaimer, the term of this patent is extended or adjusted under 35 U.S.C. 154(b) by 346 days.

(21) Appl. No.: 18/550,802

(22) PCT Filed: Mar. 22, 2022

(86) PCT No.: PCT/IT2022/050064
§ 371 (c)(1),
(2) Date: Sep. 15, 2023

(87) PCT Pub. No.: WO2022/201211
PCT Pub. Date: Sep. 29, 2022

(65) Prior Publication Data

US 2024/0197649 A1 Jun. 20, 2024

(30) Foreign Application Priority Data

Mar. 22, 2021 (IT) ........................ 102021000006839

(51) Int. Cl.

| | |
|---|---|
| ***A61K 31/07*** | (2006.01) |
| ***A61K 9/06*** | (2006.01) |
| ***A61K 9/107*** | (2006.01) |
| ***A61K 47/22*** | (2006.01) |
| ***A61K 47/32*** | (2006.01) |
| ***A61K 47/38*** | (2006.01) |
| ***B82Y 5/00*** | (2011.01) |

(52) U.S. Cl.
CPC ................ *A61K 31/07* (2013.01); *A61K 9/06* (2013.01); *A61K 9/1075* (2013.01); *A61K 47/22* (2013.01); *A61K 47/32* (2013.01); *A61K 47/38* (2013.01); *B82Y 5/00* (2013.01)

(58) Field of Classification Search
None
See application file for complete search history.

(56) References Cited

U.S. PATENT DOCUMENTS 6,573,299 B1 6/2003 Petrus

FOREIGN PATENT DOCUMENTS

| | | | |
|---|---|---|---|
| EP | 2579845 B1 * | 4/2020 | ............. A61K 47/14 |
| WO | 2009084069 A2 | 7/2009 | |

OTHER PUBLICATIONS

Souto et al. (Microemulsions and nanoemulsions in skin drug delivery, Bioengineering, Apr. 5, 2022). (Year: 2022).*
International Search Report in PCT/IT2022/050064, mailed Jul. 8, 2022, 4 pages.
Search Report and Opinion in IT202100006839, mailed Dec. 2, 2021, 8 pages.
Written Opinion in PCT/IT2022/050064, mailed Jul. 8, 2022, 4 pages.

* cited by examiner

*Primary Examiner* — Melissa S Mercier
(74) *Attorney, Agent, or Firm* — ArentFox Schiff LLP

(57) ABSTRACT

A method for the production of a topical ophthalmic preparation useful as a tear substitute and agent for the treatment of the computer vision syndrome and the related product are disclosed. In addition to the water-soluble ingredients typical of aqueous eye drops or gels, the preparation also contains a stable micellar solution (or microemulsion) of lutein with vitamin E TPGS.

12 Claims, No Drawings

WATER-SOLUBLE TOPICAL OPHTHALMIC PREPARATION CONTAINING LUTEIN AND PRODUCTION METHOD THEREOF

CROSS-REFERENCE TO RELATED APPLICATIONS

This application is a 35 U.S.C. § 371 National Phase of PCT Application No. PCT/IT2022/050064, filed Mar. 22, 2022, which claims priority to Italian Application No. 102021000006839, filed Mar. 22, 2021, the disclosures of which are hereby incorporated by reference herein.

FIELD OF THE INVENTION

The present invention relates to a water-soluble topical ophthalmic preparation containing lutein and the production method thereof. More particularly, the invention relates to a specific process for the production of a tear substitute which, in addition to the necessary viscosifying and mucomimetic agents and the usual additives typical of aqueous eye drops, such as buffers, osmoprotective or isotonizing agents, chelating and possibly antimicrobial agents, also contains a fat-soluble active ingredient with a high antioxidant and photoprotective power, lutein, in combination with a well-known emulsifier, vitamin E TPGS. A specific sequential preparative method makes it possible to obtain a stable micellar solution (or microemulsion) suitable for topical ophthalmic administration.

BACKGROUND OF THE INVENTION

The organ of sight, which has the function of capturing the luminous radiations coming from the external world to transform them into nerve impulses, used for perceptive purposes such as vision and reflexes, is separated from the external environment by the tear film, a layer of liquid in turn composed of several layers. The tear film is continuously and uniformly distributed on the ocular surface by the closure of the eyelids and has a crucial function in maintaining the homeostasis of the ocular surface. It allows adequate lubrication of the corneal epithelium by reducing friction with the eyelids, allows the transport and diffusion of vital molecules (oxygen, carbon dioxide, ions, mucins, lipids) for the survival of the epithelia and cornea. It also possesses a marked antibacterial activity, thanks to the presence of some enzymes and, finally, it guarantees the exchange and keeps the ocular surface clean, removing impurities coming from the environment, metabolic waste and desquamated cells.

From the outside towards the inside, the layers of the tear film are as follows:

1) a thin superficial lipid layer, produced by the meibomian glands, which has the function of delaying the evaporation of the underlying aqueous layer, preventing the escape of tears from the eyelid margins and maintaining hydration during the hours of sleep;
2) an intermediate aqueous layer, containing different molecules (electrolytes, proteins, amino acids, organic acids) with enzymatic and antibacterial functions, which provide for the protection, nutrition and replacement of the epithelium, as well as reducing the friction of blinking and washing the ocular surface of the numerous impurities that are deposited there;
3) an innermost mucous layer, consisting of mucin, with a marked hydrophilicity, the presence of which allows the aqueous layer to spread over the otherwise highly hydrophobic corneal epithelium.

The stability of the tear film is therefore the result of the balance of different components, the alteration of which can lead to the onset of lacrimal dysfunction syndrome, also known as dry eye syndrome, and other ophthalmic diseases.

The aqueous layer of the tear film is constantly subjected to evaporation, which is continuously compensated by the tear secretion. When this compensatory secretion for some reason is reduced or insufficient, the symptoms of dry eye disease appear, consisting of a dehydration that involves continuous ocular discomfort, with foreign body sensation in the eye, itching, burning, difficulty opening your eyes, desire to wash or rub your eyes, discomfort when looking at the light, eyestrain during the day. Reddened and less luminous eyes are almost always a sign of a bad state of hydration of the ocular surface.

Dry eye due to reduced tear production is distinguished more precisely into two main subclasses: dry eye associated with Sjögren's syndrome (SSDE), a chronic inflammatory disease of an autoimmune nature, and dry eye not caused by Sjögren's syndrome, which collects the cases of lacrimal dysfunction in which the systemic autoimmune aspects characteristic of the SSDE have been excluded.

Also some ocular surface diseases can change the amount and composition of tear fluid. The most obvious case is that of blepharitis, in which the inflammation of the eyelid creates alterations in the production of the secretion of the meibomian glands, with consequent alteration of the tear film. Even the incorrect use of contact lenses, of any type, worn for too many hours during the day, can cause an alteration of the tear film.

Another problem, which appeared in more recent times, which shares some of the symptoms associated with dry eye syndrome, is caused by the massive use of smartphones and computers, and of all screens that emit light radiation that interact with the different parts of the eye. The latter has to "filter" these radiations, the artificial component of which called "blue light" is the most harmful. Blue light is emitted in a more or less evident way from all light sources, especially from cold light sources, such as LED light, and is used in a wide-spread way. Exposure to radiation corresponding to wavelengths in the range between 380 and 500 nanometers, which also include a part of the near ultraviolet, is in fact harmful to the eye, and is associated with an increase in ocular inflammation because determines an increase in the production of oxygen free radicals, which contribute to the progressive degeneration of the retina.

In addition, during the use of the computer the blinking frequency is significantly reduced, and consequently there is an increase in the exposure time of the ocular surface, and a greater evaporation of tear fluid.

All this has led the American Optometric Association to define the so-called "computer vision syndrome" (CVS), which is currently a widespread problem, with a huge number of people affected all over the world, and a pool of potential very high patients. Symptoms are varied and are of a visual, neurological and musculoskeletal type; they do not necessarily occur all together, they vary greatly from person to person and are grouped into external and internal symptoms. The former include burning, irritation, tearing, dryness, and appear to be related to poor lacrimation problems, while the latter include eye fatigue, headache, eye pain, double vision and blurry vision, and are generally related to visual problems in strict sense (refractive, accommodative or binocular).

To contribute to the improvement of dry eyes, numerous formulations of tear substitutes (artificial tears) have been introduced on the market, to be applied periodically by instillation on the cornea or in the conjunctival fornix, with the aim of providing appropriate therapeutic means for alleviate symptoms. Specifically, the main objectives of a dry eye treatment are to improve ocular comfort and quality of life, and to restore the normal homeostatic balance of the ocular surface and tear film. Although symptoms can rarely be completely eliminated, they can often be improved.

The normal tear substitutes, consisting of artificial tears, ointments and gels, generally function as lubricants of the ocular surface, and the numerous substances used for this purpose as viscosifying agents do not have a real pharmacological action: the only activity attributable to them with certainty is lubrication. As regards the computer vision syndrome, in any case, the use of electronic screens for periods of more than 4-5 hours a day is not recommended. Again, if necessary, it is recommended to instill ocular lubricants to reduce the burning sensation and dryness.

It is known that lutein and its stereoisomer zeaxanthin, members of the xanthophyll family of carotenoids (β, ε-caroten-3,3'-diol), are antioxidant molecules that the human body is unable to synthesize, the absorption of which, therefore, depends on the consumption of certain fruits, vegetables or animal products such as eggs. As reported in the literature, these antioxidant molecules are highly concentrated in the retina and macula of the human eye (Roberts J. E., Dennison J., The Photobiology of Lutein and Zeaxanthin in the Eye, *J. Ophthalmol.,* 2015: 687173). Absorption of lutein has also been reported to improve visual acuity and slow down progression of age-related macular degeneration (AMD) (Moschos, M. M. et al., Effect of carotenoids dietary supplementation on macular function in diabetic patients. *Eye Vis.* 2017, 4, 23; Gong, X. et al. Effects of the Macular Carotenoid Lutein in Human Retinal Pigment Epithelial Cells, *Antioxidants* 2017, 6, 100).

Thanks to its physical property of absorbing light in the wavelengths typical of blue light and UVA/UVB/UVC rays, lutein exerts a barrier effect that protects the eye and the photoreceptive structures of the retina from light insults, such as those coming from the sunrays and from computer screens, smartphones or other electronic devices. Its characteristic structure with nine double bonds:

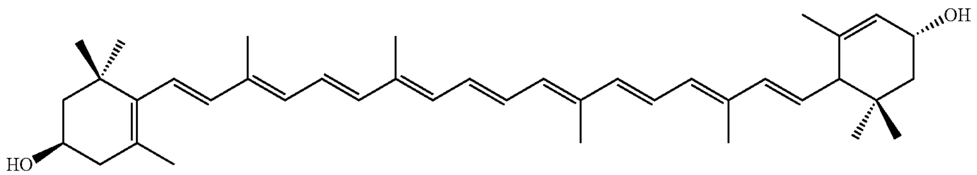

Lutein is in fact responsible for the absorbance of some wavelengths of light and the emission of other wavelengths. In particular, lutein and zeaxanthin absorb visible blue light (400-500 nm) with an absorption peak at 440 nm. It has been shown by the cited literature that age-related or diet-related loss of lutein and zeaxanthin increases UV-induced damage to the eye, and that dietary supplementation with these carotenoids has a protective effect against induced damage from UV radiation to the retina.

Although lutein is widely used in the formulation of specific food supplements in the ophthalmic field, it is not commercially available in preparations for topical ophthalmic use, i.e. to be administered directly into the eye in the form of eye-drops or aqueous-based gel, or in the form of ointment or ophthalmic ointment. To formulate a lipophilic molecule such as lutein in a topical ophthalmic product it is, in fact, necessary to convey it in an oil-in-water emulsion, which is stable over time, in order to guarantee its conservation for the times envisaged for a commercial product of this type, and without penalizing the bioavailability of the active ingredient.

The U.S. Pat. No. 6,573,299 B1 (Petrus) discloses a topical ophthalmic gel composition for application to the eyelids and in the orbital area, which composition may comprise lutein and tocopherol acetate, as well as carboxyvinyl polymers (carbomer) as a gelling agent. The composition exploits a penetration enhancer to have the actives penetrate into the underlying tissues and into the vascular network of the orbit.

The international patent publication WO2009/084069 (Lio Farmaceutici S.r.l.) discloses ophthalmic compositions in the form of aqueous solutions or gels, in which lutein is encapsulated in liposomes/cerasomes. The compositions may also comprise hyaluronic acid (salts) and buffers.

A known and widely used emulsifying agent also in the ophthalmic sector is an amphiphilic derivative of vitamin E (specifically, of the most widespread component of vitamin E, β-tocopherol), consisting of a hydrophilic polar head formed by a polyethylene glycol chain, connected to the tocopherol structure by the diester bridge of succinic acid.

A known and widely used emulsifying agent also in the ophthalmic sector is an amphiphilic derivative of vitamin E (specifically, of the most widespread component of vitamin E, β-tocopherol), consisting of a hydrophilic polar head formed by a polyethylene glycol chain, connected to the tocopherol structure by the diester bridge of succinic acid.

nutraceutical preparations, being able to emulsify or help solubilize a wide range of immiscible water-oil compounds and other poorly soluble compounds (Maya et al., Pharmaceutical Profile of Alpha-tocopherol—A Brief Review, *Int. J. Pharma. Chem. Sci.* 2012 1 (3): 1023-1039).

The use of TPGS in the ophthalmic field is described, for example, in U.S. Pat. No. 5,886,030 (Alcon Laboratories Inc.), which proposes to use it in ophthalmic formulas with non-steroidal anti-inflammatory active ingredients (NSAIDs), with the function of reducing the effect irritant of NSAIDs when applied directly to the cornea, and also to improve its solubility in aqueous phases.

Furthermore, as regards the problem of lipophilic active ingredients, the use of TPGS as a specific emulsifier has been proposed, for example, in the European patent EP 2197461 B1 (Aurinia Pharmaceuticals), where it is formulated together with another surfactant (a PEG alkyl-arylether, octoxynol-40) to obtain micellar solutions for the delivery of active principles inhibiting calcineurin, in particular cyclosporine A, in a topical ophthalmic preparation. The preparative method involves the mixing of the lipophilic active ingredient with the two surfactants in a common solvent, the evaporation of the solvent to give an almost solid material, the hydration of this material with an aqueous solution and the dissolution of the product, to give an optically transparent micellar solution.

In the same field, the European patent EP 2579845 (Medivis), discloses topical ophthalmic preparations consisting of an oil-in-water microemulsion comprising: one or more liposoluble active ingredients (which may also be lacking, in case an artificial tear is desired), an emulsifying agent consisting of d-α-tocopheryl polyethylene glycol 1000 succinate (TPGS), an oily component consisting of medium chain triglycerides (MCT) and an ophthalmologically acceptable aqueous phase. The concentration of TPGS in the product is between 0.1 and 5% by weight, the weight ratio of MCT to TPGS is between 1:2.8 and 1:3.6. Further, there are no co-surfactants present, and the average size of the particles of the oily phase dispersed in the aqueous phase is not greater than 100 nm, normally not greater than 30 nm. With the aforementioned specifications, it is reported that the preparation of the microemulsion takes place spontaneously and at room temperature, taking care to first mix the components of the oily phase (i.e. any fat-soluble active ingredient, MCTs and vitamin E TPGS), then the compo-

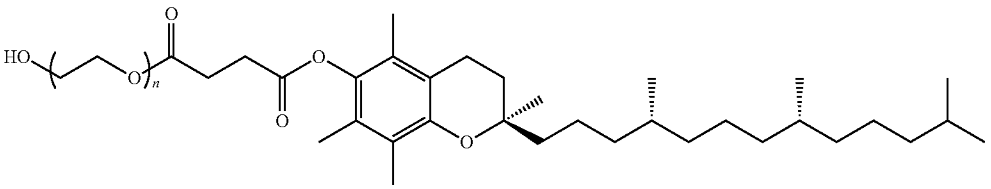

Vitamin E TPGS

This compound, whose chemical name is d-alpha-tocopheryl polyethylene glycol 1000 succinate (where 1000 refers to the chain length of the PEG), is known as vitamin E TPGS, or also with the names TPGS (the English acronym) and tocofersolan (INN).

Vitamin E TPGS shows a low critical micellar concentration and a large surface area, characteristics that make it a good emulsifier. For these reasons, this compound is considered a multi-role excipient and is widely used in nents of the aqueous phase together, and then join the two phases together, always under stirring and at room temperature.

The presence of vitamin E (α-tocopherol) in a topical ophthalmic product is certainly beneficial and well tolerated, first of all because α-tocopherol was detected in tears at the physiological concentration of 0.033-0.95 μM (Khaksari M. et al., Determination of water-soluble and fat-soluble vitamins in tears and blood serum of infants and parents by liquid chromatography/mass spectrometry, *Experimental Eye Res.* 2017 155: 54-63). Furthermore, it is confirmed that the antioxidant properties of Vitamin E are useful in case of glaucoma, cataracts, dry eye syndrome and other ocular pathologies (Ribeiro A. et al., Poloxamine micellar solubilization of alpha-tocopherol for topical ocular treatment, *Colloids Surf. B Biointerfaces* 2017 103: 550-5572013). Vitamin E, thanks to its antioxidant properties, also has photoprotective functions. In fact, the literature data indicate that Vitamin E is able to filter UV rays (range of 300-400 nm, with a peak at 350 nm), and has protective effects against cell damage induced by rays. UV (Ayala M. N. and Soderberg P. G., Vitamin E can protect against ultraviolet radiation-induced cataract in albino rats, *Ophthalmic Res.* 2004, 36 (5): 264-269).

It is also known that vitamin E and lutein act together as powerful antioxidants that neutralize reactive oxygen species (ROS) induced by UV radiation. These two compounds in combination are even more useful for ocular photoprotection from UV, as they protect the eye from lipid peroxidation, which causes the oxidative degradation of lipids and the formation of free radicals: it has been shown that lutein and Vitamin E act synergistically to neutralize free radicals. In particular, the effects of lutein and vitamin E on lipid peroxidation in human lens epithelial cells after UVB irradiation were examined, and it was found that the pretreatment of cell cultures with lutein and vitamin E prior to UVB radiation exposure reduced lipid peroxidation by 47-57% compared to control epithelial cells treated with UVB only (Chitchumroonchokchai C. et al., Xanthophylls and alpha-tocopherol decrease UVB-induced lipid peroxidation and stress signaling in human lens epithelial cells, *J. Nutr.* 2004, 134 (12): 3225-32322004).

In the light of the prior art described, it is evident that it would be extremely advantageous to have an ophthalmic preparation for topical use which makes lutein easily administrable and bioavailable together with the other components, mostly water-soluble, normally used for the treatment of disorders and pathologies which require protection and lubrication of the ocular surface and internal structures of the eye.

SUMMARY OF THE INVENTION

The object of the present invention is, therefore, to provide a tear substitute containing a lipid phase composed exclusively of vitamin E-TPGS and lutein in combination. Such combination has never been used in a preparation for topical ophthalmic administration. The tear substitute must be biocompatible and suitable for use even while wearing contact lenses, must be suitable for the management and therapy of the aforementioned pathologies, so as to alleviate the symptoms shared between dry eye syndrome and CVS (irritation, burning, foreign body sensation, photophobia) thanks to its lubricating, antioxidant and photoprotective properties.

As noted, lutein, being a lipophilic molecule, is insoluble in water. In the initial stages of the experimentation connected with the present invention, preliminary tests were carried out which confirmed that lutein, added to an aqueous solution, for the most part deposits rapidly on the bottom, even if the mixture was subjected to a strong and prolonged stirring.

According to the invention, it has been found that it is possible to obtain an ophthalmic preparation containing lutein, which is biocompatible and at the same time has lubricating, antioxidant and photoprotective activity, which keeps its physico-chemical characteristics stable over time, realizing, through a particular manufacturing process, a micellar solution (or microemulsion) of lutein emulsified with vitamin E TPGS. This micellar solution based on lutein is made, according to the invention, without the use of additional lipid excipients, with the exception of a minimum amount of vitamin E-TPGS.

The aforementioned micellar solution is dispersed in an aqueous phase containing one or more viscosifying agents (rheological modifiers) and/or mucoadhesive agents, in addition to the usual isotonizing agents (osmotizing agents, tonicity-adjusting agents), buffers and any further water-soluble components. The ophthalmic preparation of the invention can be obtained by implementing a specific four-step preparation method specially developed.

It has in fact been found, according to the present invention, that in certain conditions of temperature and stirring, vitamin E-TPGS, being an amphiphilic molecule with a polar hydrophilic head and a lipophilic tail, is able to bind lutein and subsequently carry it inside an aqueous solution, in stable micellar form. The molecular characteristics of vitamin E-TPGS make it an excellent solubilizer for lutein, causing it to spontaneously form with it, under the conditions specified according to the invention, a double layer in which its hydrophilic heads are turned towards the external aqueous phase, while the hydrophobic tails that bind the lutein are turned towards the interior of the micelle, without the need for further oily components in the lipid phase.

Thanks to the thermal/mechanical energy supplied to the system during preparation, it is possible to obtain a size of the dispersed particles of less than 30 nm, generally in a range between 5 and 10 nm. The preparation has in fact a limpid aspect with a bright orange color.

The ophthalmic product for topical use of the invention can be obtained through a preparation process in four steps. In this process, in the first step a predetermined quantity of deionized water is introduced into a first vessel, to which one or more of the other water-soluble ingredients of the formulation, such as the buffer system, are added. In the second step, vitamin E TPGS is heated in a second vessel and under stirring, bringing it first to melt and then to a temperature between 90 and 170° C.; then lutein is added while maintaining high temperature and stirring speed until a homogeneous oily solution is formed. In the third step, a part of the aqueous solution of the first vessel is added to the oily solution, slowly and under stirring, after having heated it to a temperature between 80 and 90° C.; when addition is finished, heating is continued and the stirring speed is increased, keeping the temperature between 90 and 170° C. in order to obtain a stable micellar solution of vitamin E TPGS and lutein in the aqueous phase. Finally, in the fourth step, the micellar solution obtained is added to the solution remaining in the first vessel, while keeping it under stirring. Once the solution has cooled down to a temperature not exceeding 30° C., the remaining water-soluble ingredients are added one at a time, including one or more viscosifying or gelling agents. Then, the ingredients are let to completely dissolve and the product is sterilized.

By proceeding rigorously according to the indicated method, it has been possible, according to the present invention, to ensure the successful formation of a micellar aggregate vitamin E-TPGS-lutein so as to make the lutein practically "water-soluble", and to keep it stably in solution.

Thanks to the antioxidant activity and the light absorption properties in the wavelengths typical of blue light and UVA/UVB/UVC rays shown by lutein and the B-tocopherol contained in TPGS, the combination of vitamin E TPGS and lutein according to the invention affords to strengthen the barrier effect that protects the eye and the retinal photoreceptive structures from light insults, such as those coming from sunrays, computer screens, smartphones and other electronic devices.

In addition to the innovative combination of ingredients described above, the ophthalmic preparation according to the invention contains, in the aqueous phase, one or more of the usual water-soluble ingredients already known as ocular surface lubricants, such as viscosity regulating agents, mucoadhesives and corneal surface moisturizers, preferably those based on polysaccharides, such as for example hyaluronic acid (HA) or a salt thereof, and cellulose derivatives, such as carboxymethylcellulose (CMC) and hydroxypropylmethylcellulose (HPMC, hypromellose), possibly modified by cross-linking.

According to other embodiments of the present invention, the preparation containing lutein and vitamin E TPGS can be formulated in the form of eye drops, and also in the form of an ophthalmic gel, by including in the water-soluble components of the fourth step of the preparation process a polymer forming gel, such as polyacrylic acid (Carbomer), together with the related neutralizing agent.

The ophthalmic formulations of the invention have been developed both in different single-dose formats without preservatives (preservative-free) and in the multidose format version containing preservatives. Both the versions without preservative and those with preservative can be formulated with different buffer systems as needed, for example with borate, citrate or phosphate buffer. All the embodiments of the products obtainable according to the present invention can also be used while wearing contact lenses.

DETAILED DESCRIPTION OF THE INVENTION

According to a first aspect of the present invention, the specific object of the invention is a process for the production of a water-soluble ophthalmic topical preparation containing lutein which comprises, in sequence, the following operations:

Step 1 a) introducing a predetermined amount of deionized water and, optionally, the components of a buffer system and, also optionally, a predetermined amount of an ophthalmic viscosifying agent into a first stirred vessel, waiting for the complete solubilization of each of the optional ingredients;

Step 2 a) in a second stirred vessel, heating a predetermined amount of vitamin E TPGS up to a temperature of 80-90° C., preferably 80-85° C., and waiting for complete melting thereof;

b) bringing the vitamin E TPGS to a temperature of 90-170° C., preferably 150-160° C., and adding a predetermined amount of lutein, while continuing stirring until complete dissolution and formation of a homogeneous orange oily solution consisting exclusively of vitamin E TPGS and lutein;

Step 3 a) heating the water or the aqueous solution obtained from operation a) of Step 1 to a temperature of 80-90° C., preferably 80-85° C., and adding an aliquot thereof, gradually, to said second vessel, while keeping it under stirring—the aliquot to be added gradually must correspond to about 1/10 of the entire volume of the final product, for example, for a total volume of product equal to 1000 ml, a volume corresponding to about 100 ml must be added to said second vessel—it is during this operation that the product passes, by means of a phase inversion, from a water-in-oil emulsion to an oil-in-water emulsion;

b) once the addition is complete, increasing the stirring speed while maintaining the temperature in the 90-170° C. range until a completely clear and op

Step 4 a) adding the solution of Step 3 to the remaining water or aqueous solution obtained from operation a) of Step 1;

b) after verifying that the temperature has fallen down to, or below, 30° C., adding to the stirred vessel the other water-soluble ingredients of the topical ophthalmic preparation being produced, one at a time and in predetermined quantities, including one or more viscosifying agents and/or mucoadhesives, waiting for the complete solubilization of each;

c) sterilizing the product thus obtained.

According to some specific embodiments of the invention, said topical ophthalmic preparation is in liquid form, i.e. an eye drop to be administered in drops. In this case, in operation a) of Step 1, in addition to deionized water, also the components of a buffer system are introduced into said first vessel, said components being, preferably but not necessarily, boric acid and sodium tetraborate, or citric acid and sodium citrate, or the components of a phosphate buffer. In the event that the ophthalmic viscosifying agent is cross-linked hyaluronic acid (HA-CK), this ingredient is added after the two components of the buffer system, in Step 1.

In addition or alternatively, the one or more viscosifying and/or mucoadhesive agents, which are preferably selected from hyaluronic acid or one of its salts (HA), carboxymethylcellulose (CMC) and cross-linked carboxymethylcellulose (CMC-CK), is/are incorporated into the prepared during operation b) of Step 4.

Sodium hyaluronate or hyaluronic acid (HA) is a natural polysaccharide consisting of a particular structure formed by repeated units of D-glucuronic acid and N-acetylglucosamine, which, thanks to its well-known hygroscopic properties, enhances lubrication, hydration and protection the ocular surface. HA stabilizes both the aqueous layer of the tear film and, in the presence of contact lenses, the aqueous layer of the pre-lens tear film (PrLTF). In addition, the mucoadhesive properties and the lubricating action of hyaluronic acid assist the physiological repair processes of the corneal epithelium.

Actually, in the healthy eye, the presence of an intact mucous layer is essential, as it converts the corneal epithelium from a hydrophobic to a hydrophilic surface, protects the epithelia from eyelid rubbing, thanks to its viscoelastic properties, prevents bacterial adhesion and allows the regular and uniform distribution of the lipid layer of the tear film on the aqueous layer, thus reducing the surface tension. If the production of mucus is reduced, for example due to damage to the goblet cells of the cornea, the distribution of the same on the ocular surface is compromised, with consequent reduction of contact between the tear film and the ocular surface, loss of film stability and formation of dry areas.

It follows that the symptomatological efficacy of a tear substitute is closely related both to its ability to remain on the ocular surface, and to its mucomimetic and mucoadhesive characteristics. For these reasons macromolecular compounds are added to the tear substitutes which act as viscosity regulating agents, which, in addition to washing away and diluting the toxic or irritating substances present in the tear film, hydrate the gelatinous mucin formations. These compounds also increase the holding time, offering a longer period of comfort to the user. Furthermore, viscosifying agents protect the epithelium of the ocular surface.

With specific reference to hyaluronic acid, numerous experiments have been carried out with the aim of chemically modifying its molecule in order to further improve its properties. The most used chemical strategy to modify HA is cross-linking, by direct addition of side chains or by adding spacer arms, which can then form stabilizing bonds between the molecules of HA. In this way there is a greater viscoelasticity, which extends the contact time of HA with the ocular surface.

Carboxymethylcellulose (CMC) is one of the most widely used viscosity regulators in the ophthalmic field. This polymer is often added to medical devices for its property of thickening and stabilizing the tear film on the corneal surface, hydrating it and creating a protective, transparent and viscoelastic shield capable of extending the lifetime of the tear film on the cornea between blinks (break-up time). The break-up time is typically shortened in dry eye conditions. CMC also has cytoprotective activity on the ocular surface when applied before contact lenses. In addition, subacute and chronic toxicity studies have reported the absence of adverse effects induced by CMC, confirming its safety.

A cross-linked variant (CMC-CK, cross-linked) is also commercially available for carboxymethylcellulose, the toxicological profile of which has been judged equivalent to that of CMC by the European Commission.

According to the aforementioned first embodiments of the invention, the ophthalmic solution obtained from operation b) of Step 4 of the process is filtered at 0.2 μm to make it sterile, and sent for packaging in suitable containers. According to other specific embodiments of the invention, in which the topical preparation is in the form of an ophthalmic gel, in operation b) of Step 4 a predetermined quantity of a gelling agent, preferably carboxyvinyl polymer (Carbomer), is added to the stirred vessel through a sieve. The gelling agent is allowed to soak and subsequently disperse, while continuing stirring until a lump-free dispersion is obtained. It is then neutralized with a neutralizing agent, gently continuing the stirring.

In the case of the production of gel preparations according to the invention, the sterilization operation c) of Step 4 is carried out by subjecting the product obtained to autoclaving or to treatment with gamma rays.

It should be noted that a fundamental step of the proposed method is to heat the solution obtained in Step 1 to between 80 and 90° C. before a part of it is added to the vitamin E TPGS-lutein aggregate of Step 2. If this operation is performed at a lower temperature, there would be a thermal shock in the vitamin E TPGS-lutein aggregate, which would no longer lead to the production of a clear solution but to a cloudy liquid. Going on with the production process and filtering at 0.2 μm, a transparent solution would be obtained, but in any case such solution would not comply with the specifications, as the finished product could be colorless. This result indicates a loss of the vitamin E TPGS-lutein aggregate.

In Step 2 the critical points are as follows:

- it is necessary to make sure that the total phase change occurs in vitamin E TPGS: this indicates that the molecule is ready to bind lutein in the best way;
- after adding all the lutein, the temperature must be kept between 80 and 170° C. by increasing the stirring speed for at least 1 minute.

Proceeding with the following operations without being sure of compliance with the two conditions indicated would result in a product not having a clear appearance and not being free of precipitates.

In Step 3, if all the previous steps of the preparation method have been followed, it becomes crucial not to reduce the agitation speed, and keep the temperature between 80 and 170° C. until the micellar solution becomes transparent.

Compliance with all the specified operating conditions is necessary in order to obtain a product that is not only compliant but also stable over time. In this regard, it is important to note that it is not sufficient to add to the solvent all the components declared in the order described because, despite the use of vitamin E-TPGS as an emulsifier, a final product would be obtained in which the lutein would deposit on the bottom as an insoluble precipitate.

The preparation method according to the invention does not cause the disappearance of the lutein in solution, as is demonstrated by the fact that the orange color of the product remains present despite the treatments to which it is subjected during some steps of the preparation, in particular, during the steps at high temperature and during the filtration of the semi-finished product. As a matter of fact, if the temperature somehow compromised the molecular structure of lutein by breaking the chain of double bonds responsible for the absorption of visible blue light between 400-500 nm (Roberts et al., 2015, already cited) and the consequent emission of the corresponding wavelengths (ranging from yellow to red, passing, actually, through orange), already in the semi-finished product (i.e., before filtration) it would not be possible to obtain the characteristic color of lutein. It would not be obtained even if filtration at 0.2 μm mechanically blocked the micellar solution of the vitamin E TPGS-lutein aggregate.

The product obtained by applying the production process of the invention has the following characteristics:

| PHYSICO-CHEMICAL AND MICROBIOLOGICAL CHARACTERISTICS | |
|---|---|
| Appearance | Clear liquid without precipitates |
| Color | From light yellow to intense orange |
| Odor | Odorless |
| pH | 6.80-7.60 pH units |
| Osmolality | 250-350 mOsm/kg |
| Density | 0.975-1.025 g/cm$^3$ |
| Viscosity | 2.00-6.00 cP |
| Sterility | Sterile |

According to a further aspect, the present invention relates to a topical ophthalmic preparation consisting of a stable micellar solution (microemulsion) of vitamin E TPGS and lutein, suspended in an aqueous phase comprising viscosifying and/or mucoadhesive agents, or gelling agents, together with other pharmacologically acceptable excipients.

Preferred embodiments of the described preparation are those in which the viscosifying and/or mucoadhesive agents are selected from hyaluronic acid or its salts (HA), cross-linked hyaluronic acid (HA-CK), carboxymethylcellulose (CMC), cross-linked carboxymethylcellulose (CMC-CK) and their mixtures. Other preferred embodiments are those in aqueous gel, in which the gelling agent is based, for example, on a carboxyvinyl polymer (Carbomer).

A generic example of formulation of an obtainable ophthalmic solution according to the present invention may have the composition indicated in the following table.

| QUALITATIVE AND QUANTITATIVE COMPOSITION | | |
|---|---|---|
| INGREDIENTS | Function | % w/w |
| Deionized water | Solvent | q.s. to 100 g |
| Buffer system | pH regulator | q.s. to pH 6.80-7.60 |
| Disodium edetate)EDTA) | Chelating agent | 0-1 |
| Sodium chloride, glycerol or equivalent | Isotonicity stabilizer | q.s. to 250-350 mOsm/kg |
| Optionally cross-linked poly-saccharide | Viscosifyer, mucoadhesive, moisturizer | <1 |
| Vit. E TPGS | Lutein solubilizer, antioxidant | 0.05-10.0 |
| Lutein | Photoprotective agent, antioxidant | 0.001-0.5 |
| Antimicrobial agent | Preservative | 0-0.1 |

The above is an example of the formulation of the ophthalmic product in eye drops, based on a stable micellar solution of vitamin E TPGS and lutein according to the invention. A similar example of a gel product can be obtained by eliminating the buffer system and the polysaccharide from the previous formulation and inserting a hydrophilic gelling polymer in its place, in addition to any related neutralizing agent.

EXAMPLES

Some specific embodiments of the formulation method and the related products according to the invention are described below by way of example but not of limitation, together with the results of the experiments carried out.

It should be emphasized that the preparation method proposed for products in liquid form always follows the same steps, except for the formulations, with or without preservative, containing HA-CK. For this type of formulations the difference concerns one of the steps of Step 1, in which HA-CK can also be added immediately after the addition of the components that determine the buffer. This practice can improve and speed up its passage into solution, as suggested by the manufacturer.

Examples 1 and 2

Below are reported the compositions of two eye drops preparations, with and without preservative, with lutein solubilized with vitamin E TPGS in citrate buffer, which have sodium hyaluronate (HA) the viscosifying agent.

| Lutein, HA and citrate buffer lubricating solution | |
|---|---|
| INGREDIENTS | % w/w |
| Deionized water | 97.166 |
| Citric acid | 0.135 |
| Sodium citrate | 1.720 |
| Disodium edetate | 0.100 |
| Lutein | 0.005 |
| Vitamin E TPGS | 0.200 |
| Sodium hyaluronate | 0.100 |
| Sodium chloride | 0.300 |
| Sodium hydroxide 32% | 0.234 |
| Microglicin 50 | 0.040 |

| Lutein, HA and citrate buffer lubricating solution, without preservatives | |
|---|---|
| INGREDIENTS | % w/w |
| Deionized water | 97.474 |
| Citric acid | 0.008 |
| Sodium citrate | 1.720 |
| Disodium edetate | 0.100 |
| Lutein | 0.005 |
| Vitamin E TPGS | 0.200 |
| Sodium hyaluronate | 0.100 |
| Sodium chloride | 0.360 |
| Sodium hydroxide 32% | 0.033 |

The specific procedure through which the two preparations in question were obtained is as follows:

Step 1

Deionized water is weighed, placed in a suitable vessel, and placed under stirring;

the components of the buffer, citric acid and sodium citrate, are weighed one at a time and introduced into the vessel under stirring, in the order indicated;

stirring is continued until complete solubilization.

Step 2

Vitamin E TPGS is weighed and placed in a suitable borosilicate glass vessel, placed on a magnetic stirrer with a heating plate;

a magnet is inserted into the vessel and stirring is activated without exceeding 500 rpm;

vitamin E-TPGS is heated bringing it to 80° C., and it is waited until it changes state, passing from waxy solid to fluid;

lutein is weighed in a special vessel;

the temperature of vitamin E-TPGS is brought to 150-160° C. and lutein is added in the vessel with vitamin E TPGS, making sure that it dissolves completely inside vitamin E TPGS and that the mixture becomes intense orange in color and devoid of undissolved dark corpuscles;

once all the lutein has been added, wait another minute is waited while increasing the stirring speed to 1000 rpm, to be sure that all the lutein is bound to vitamin E TPGS, forming a stable aggregate.

Step 3

Add, a little at a time, an aliquot of the aqueous solution produced in Step 1, heated to 80° C., to the oily phase vitamin E TPGS-lutein, checking in advance that the temperature is not lower than 80° C. (upon the addition of the aqueous solution, a change of the oily phase will initially be obtained, which, from a translucent orange gel will partly return to solidify);

at the end of adding the whole aliquot of the solution of Step 1, the stirring speed is increased from 1000 to 1500 rpm, keeping the temperature between 150 and 160° C. until there are no more undissolved parts of aggregate vitamin E TPGS-lutein;

stirring and heating are stopped only when the orange solution is completely clear.

Step 4

The solution produced in Step 3 is poured into the solution produced in Step 1; after having verified that the solution temperature does not exceed 30° C., the following steps are taken;

the following ingredients are weighed: disodium edetate, sodium chloride, sodium hyaluronate, (optionally Microglicin 50);

add the ingredients just weighed, one at a time, to the stirring tank, respecting the order mentioned above;

the solution is left under stirring until the components just added are completely dissolved;

the finished product is filtered at 0.2 μm, before filling it in the appropriate primary packaging, to make it sterile.

Examples 3 and 4

Below are the compositions of two eye drops preparations, with and without preservative, with lutein solubilized with vitamin E TPGS in citrate buffer, which have cross-linked sodium hyaluronate (HA-CK) as the viscosifying agent.

Lutein, HA-CK and citrate buffer lubricating solution

| INGREDIENTS | % w/w |
|---|---|
| Deionized water | 97.165 |
| Citric acid | 0.135 |
| Sodium citrate | 1.720 |
| Disodium edetate | 0.100 |
| Lutein | 0.005 |
| Vitamin E TPGS | 0.200 |
| Sodium hyaluronate CK | 0.100 |
| Sodium chloride | 0.300 |
| Sodium hydroxide 32% | 0.235 |
| Microglicin 50 | 0.040 |

Lutein, HA-CK and citrate buffer lubricating solution, without preservatives

| INGREDIENTS | % w/w |
|---|---|
| Deionized water | 97.474 |
| Citric acid | 0.008 |
| Sodium citrate | 1.720 |
| Disodium edetate | 0.100 |
| Lutein | 0.005 |
| Vitamin E TPGS | 0.200 |
| Sodium hyaluronate CK | 0.100 |
| Sodium chloride | 0.360 |
| Sodium hydroxide 32% | 0.033 |

The procedure through which the two preparations in question were obtained is the same, respectively, of Examples 1 and 2, except for the fact, already mentioned, that sodium hyaluronate CK is added in Step 1, and not in the final step.

Examples 5 and 6

Below are the compositions of two eye drops preparations, with and without preservative, with lutein solubilized with vitamin E TPGS in citrate buffer, which have carboxymethylcellulose (CMC) as the viscosifying agent.

Lutein, CMC and citrate buffer lubricating solution

| INGREDIENTS | % w/w |
|---|---|
| Deionized water | 96.874 |
| Citric acid | 0.135 |
| Sodium citrate | 1.720 |
| Disodium edetate | 0.100 |
| Lutein | 0.005 |
| Vitamin E TPGS | 0.200 |
| Carboxymethylcellulose | 0.400 |
| Sodium chloride | 0.290 |
| Sodium hydroxide 32% | 0.236 |
| Microglicin 50 | 0.040 |

Lutein, CMC and citrate buffer lubricating solution, without preservatives

| INGREDIENTS | % w/w |
|---|---|
| Deionized water | 97.173 |
| Citric acid | 0.008 |
| Sodium citrate | 1.720 |
| Disodium edetate | 0.100 |
| Lutein | 0.005 |
| Vitamin E TPGS | 0.200 |
| Carboxymethylcellulose | 0.400 |
| Sodium chloride | 0.360 |
| Sodium hydroxide 32% | 0.034 |

The procedure through which the two preparations in question were obtained is the same, respectively, of Examples 1 and 2.

Examples 7 and 8

Below are the compositions of two eye drops preparations, with and without preservative, with lutein solubilized with vitamin E TPGS in citrate buffer, which have cross-linked carboxymethylcellulose (CMC-CK) as the viscosifying agent.

Lutein, CMC-CK and citrate buffer lubricating solution

| INGREDIENTS | % w/w |
|---|---|
| Deionized water | 96.874 |
| Citric acid | 0.135 |
| Sodium citrate | 1.720 |
| Disodium edetate | 0.100 |
| Lutein | 0.005 |
| Vitamin E TPGS | 0.200 |
| Carboxymethylcellulose-CK | 0.400 |
| Sodium chloride | 0.290 |
| Sodium hydroxide 32% | 0.236 |
| Microglicin 50 | 0.040 |

| Lutein, CMC-CK and citrate buffer lubricating solution, without preservatives | |
|---|---|
| INGREDIENTS | % w/w |
| Deionized water | 97.173 |
| Citric acid | 0.008 |
| Sodium citrate | 1.720 |
| Disodium edetate | 0.100 |
| Lutein | 0.005 |
| Vitamin E TPGS | 0.200 |
| Carboxymethylcellulose-CK | 0.400 |
| Sodium chloride | 0.360 |
| Sodium hydroxide 32% | 0.034 |

The procedure through which the two preparations in question were obtained is the same, respectively, of Examples 1 and 2.

Examples 9 and 10

Below are the compositions of two eye drops preparations, with and without preservative, with lutein solubilized with vitamin E TPGS in citrate buffer, which have a carboxyvinyl polymer as the gelling agent.

| Lutein lubricating gel | |
|---|---|
| INGREDIENTS | % w/w |
| Deionized water | 94.107 |
| Lutein | 0.005 |
| Vitamin E TPGS | 0.200 |
| Disodium edetate | 0.100 |
| Sorbitol | 5.000 |
| Carbomer | 0.250 |
| Sodium hydroxide 32% | 0.298 |
| Microglicin 50 | 0.040 |

| Lutein lubricating gel, without preservative | |
|---|---|
| INGREDIENTS | % w/w |
| Deionized water | 94.132 |
| Lutein | 0.005 |
| Vitamin E TPGS | 0.200 |
| Disodium edetate | 0.100 |
| Sorbitol | 5.000 |
| Carbomer | 0.250 |
| Sodium hydroxide 32% | 0.313 |

The specific procedure through which the two gel preparations were obtained is similar, respectively, to that of Examples 1 and 2, except for some sequences of Steps 1 and 4, which are reported below.

Step 1

Deionized water is weighed, introduced into a suitable vessel, and placed under stirring.

Steps 2 and 3

As in Example 1.

Step 4

The solution produced in Step 3 is poured into the remaining deionized water in Step 1, checking that the temperature of the solution does not exceed 30° C.;

the following ingredients are weighed: disodium edetate, sorbitol, sodium hyaluronate (optionally Microglicin 50);

the ingredients just weighed are added one at a time to the stirred vessel, respecting the order mentioned above;

the solution is left under stirring until the components just added are completely dissolved;

Carbomer is added a little at a time through a sieve, and its wetting and consequent dispersion in the solution monitored is expected, bringing the stirring speed to about 800-1200 rpm; stirring is continued for about 20 minutes or until a lump-free dispersion is achieved;

32% sodium hydroxide (the neutralizing agent) is added little by little while gently stirring, mixing until a homogeneous viscous system is obtained;

the finished product is subjected to gamma irradiation or autoclaving, before filling in the appropriate primary packaging, to make it sterile.

Experimentation on the Product

In order to experimentally demonstrate the presence of lutein in the final product, the concentration data of the total carotenoids (intended as lutein and zeaxanthin) present in the finished product were obtained from some product samples prepared according to the method of the invention. The analysis made use of the spectrophotometric technique, exploiting the absorption peak at 446 nm.

The main purpose of the analysis was to demonstrate with experimental data the presence or absence of lutein in the finished product and, as a secondary purpose, to quantify lutein in order to be able to decide which initial concentration to use in order to obtain proportionally in the product the final concentration desired.

The analysis was conducted on three different types of solutions produced according to the invention, containing the same initial concentration of lutein, equal to 0.005% w/w, but different excipients.

The data obtained are shown below.

Type of sample Ophthalmic solution
Identification of the sample L.S. Lutein HA, citrate buffer and microglicin (Batch No. PR172/20)
Test Results

| PARAMETER | M.U. | VALUE U(±) | LIMIT | ANALITICAL TECHNIQUE |
|---|---|---|---|---|
| Raw material (expressed as total carotenoids) Internal Method - PT 44 rev. 1 2020 | % | 0.0029 | — | Spectrophotometry |

The value of raw material (expressed as total carotenoids) refers to the % of total carotenoids determined in the raw material (batch S2017180) equal to 43.92%

| Type of sample Ophthalmic solution<br>Identification of the sample L.S. Lutein HA, citrate buffer and microglicin (Batch No. PR173/20)<br>Test Results | | | | |
|---|---|---|---|---|
| PARAMETER | M.U. | VALUE U(±) | LIMIT | ANALITICAL TECHNIQUE |
| Raw material (expressed as total carotenoids) Internal Method - PT 44 rev. 1 2020 | % | 0.0036 | — | Spectrophotometry |

The value of raw material (expressed as total carotenoids) refers to the % of total carotenoids determined in the raw material (batch S2017180) equal to 43.92%

| Type of sample Ophthalmic solution<br>Identification of the sample L.S. Lutein HA-CK, citrate buffer and microglicin (Batch No. PR174/20)<br>Test Results | | | | |
|---|---|---|---|---|
| PARAMETER | M.U. | VALUE U(±) | LIMIT | ANALITICAL TECHNIQUE |
| Raw material (expressed as total carotenoids) Internal Method - PT 44 rev. 1 2020 | % | 0.0033 | — | Spectrophotometry |

The value of raw material (expressed as total carotenoids) refers to the % of total carotenoids determined in the raw material (batch S2017180) equal to 43.92%

As already hypothesized, the above results confirm the thesis that the production process does not eliminate lutein.

In the finished product, lutein, intended as a raw material expressed as total carotenoids, averaged around 0.0033%. This result should not be considered with respect to the starting quantity added to the solution, equal to 0.005% w/w, but taking into account the fact that the total carotenoids in the raw material are equal to 43.92% and not 50%. The trend observed is, therefore, an average loss of product of about 25%. Thus, the data obtained allows to establish upstream, according to the present invention, the initial percentage of lutein to use in order to obtain the desired quantity in the finished product.

In conclusion, the invention makes it possible to add to the performance of the usual topical ophthalmic preparations for artificial tears, or of products for the treatment of the computer vision syndrome, also the benefits of lutein and vitamin E contained in the relative emulsifier. The resulting component exerts, in addition to the usual lubricating action, also a photoprotective action, acting as a filter of the light that enters the eye, and at the same time antioxidant, because it is able to neutralize the reactive oxygen species (ROS) induced by UV rays.

The present invention has been described with reference to some specific embodiments thereof, but it is to be understood that variations or modifications may be made to it by those skilled in the art, without departing from the scope of protection as defined in the appended claims.

The invention claimed is:

1. A process for the production of a water-soluble ophthalmic topical preparation containing lutein, said process comprising, in sequence, the following operations:

Step 1:

a) introducing a predetermined amount of deionized water and, optionally, the components of a buffer system and, also optionally, a predetermined amount of an ophthalmic viscosifying agent into a first stirred vessel, waiting for the complete solubilization of the optional ingredients;

Step 2:

a) in a second stirred vessel, heating a predetermined amount of vitamin E tocopherol polyethylene glycol succinate (TPGS) up to a temperature of 80-90° C., and waiting for complete melting thereof;

b) bringing the vitamin E TPGS to a temperature of 90-170° C. and adding a predetermined amount of lutein, while continuing stirring until complete dissolution and formation of a homogeneous orange oily solution, consisting exclusively of vitamin E TPGS and lutein;

Step 3:

a) heating the water or the aqueous solution obtained from operation a) of Step 1 to a temperature of 80-90° C. and adding an aliquot thereof equal to about 10% by volume of the final product, gradually, to said second vessel, while keeping it under stirring;

b) once the addition is complete, increasing the stirring speed while maintaining the temperature in the 90-170° C. range until a completely clear and optically homogeneous orange liquid is obtained; and Step 4:

a) adding the solution of Step 3 to the remaining water or aqueous solution obtained from operation a) of Step 1;

b) after verifying that the temperature has fallen down to or below, 30° C., adding to the stirred vessel other optional water-soluble ingredients of the topical ophthalmic preparation being produced, one at a time and in predetermined quantities, said optional water-soluble components comprising one or more viscosifying agents and/or mucoadhesives, waiting for the complete solubilization thereof;

c) sterilizing the product thus obtained.

2. The production process according to claim 1, wherein said topical ophthalmic preparation is in liquid form, and wherein the composition further comprises a buffer system in step 1a.

3. The production process according to claim 1, wherein, in said operation a) of Step 1, a predetermined amount of cross-linked hyaluronic acid (HA-CK) is also introduced into said first stirred vessel.

4. The production process according to claim 1, wherein said one or more viscosifying and/or mucoadhesive agents of said operation b) of Step 4 comprise hyaluronic acid or a salt thereof (HA), or carboxymethylcellulose (CMC) or cross-linked carboxymethylcellulose (CMC-CK).

5. The production process according to claim 1, wherein said sterilization operation c) of Step 4 is carried out by filtering the product obtained through a 0.2 μm filter.

6. The production process according to claim 1, wherein the topical ophthalmic preparation is in the form of a gel; wherein step 4b further comprises a predetermined amount of a gelling agent added to the stirred vessel through a sieve, while continually stirring to obtain a lump free dispersion, and followed by neutralizing the dispersion with a neutralizing agent.

7. The production process according to claim 6, wherein said sterilization operation c) of Step 4 is carried out by subjecting the obtained product to autoclaving or to a treatment with gamma rays.

8. A topical ophthalmic preparation consisting of a stable micellar solution (microemulsion) of vitamin E TPGS and lutein, suspended in an aqueous phase comprising viscosifying and/or mucoadhesive agents or gelling agents, together with other ophthalmologically acceptable excipients, said preparation being obtainable as described in claim 1.

9. The topical ophthalmic preparation according to claim 8, wherein said viscosifying and/or mucoadhesive agents are selected from the group consisting of: hyaluronic acid or a salt thereof (HA), cross-linked hyaluronic acid (HA-CK), carboxymethylcellulose (CMC), cross-linked carboxymethylcellulose ((CMC)-CK) and their mixtures.

10. The topical ophthalmic preparation according to claim 8, wherein said gelling agents are based on a carboxyvinyl polymer.

11. The production process according to claim 2, wherein the components of a buffer system are one of borate, citrate and phosphate buffer.

12. The production process according to claim 6, wherein said gelling agent is a carboxyvinyl polymer.

* * * * *